United States Patent [19]
Österdahl et al.

[11] Patent Number: 6,020,536
[45] Date of Patent: *Feb. 1, 2000

[54] ABSORBENT BODY FOR ABSORBENT ARTICLES

[75] Inventors: Eje Österdahl, Västra Frölunda; Urban Widlund; Jeanette Annergren, both of Mölnlycke, all of Sweden

[73] Assignee: SCA Hygiene Products AB, Gothenburg, Sweden

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/731,390

[22] Filed: Oct. 15, 1996

Related U.S. Application Data

[62] Continuation-in-part of application No. 08/674,490, Jun. 28, 1996, abandoned, which is a continuation of application No. 08/256,190, filed as application No. PCT/SE92/00078, Feb. 10, 1992, abandoned.

[51] Int. Cl.⁷ ..................................................... A61F 13/15
[52] U.S. Cl. ......................... 604/378; 604/367; 604/358; 604/374
[58] Field of Search .................................. 604/378, 358, 604/367, 374

[56] References Cited

U.S. PATENT DOCUMENTS

| | | |
|---|---|---|
| 3,224,926 | 12/1965 | Bernardin . |
| 3,658,613 | 4/1972 | Steiger . |

(List continued on next page.)

FOREIGN PATENT DOCUMENTS

| | | |
|---|---|---|
| 0 158 914 | 10/1985 | European Pat. Off. . |
| 0 202 125 | 11/1986 | European Pat. Off. . |
| 0 217 766 | 4/1987 | European Pat. Off. . |
| 0 343 941 | 11/1989 | European Pat. Off. . |
| 0 397 110 | 11/1990 | European Pat. Off. . |

(List continued on next page.)

OTHER PUBLICATIONS

Produktliste der Fa. Weyerhauser, FQA Data for Weyerhaeuser Pulps.
By J. Casey, "Pulp and Paper Chemistry and Chemical Technology", vol. II: Papermakinbg, 1960, pp. 643–645.
By H. Kolmodin et al., "Fluff, an expanding field of application for wood fibers", Research—special section of Svensk Papperstidning, No. 12, 1981, pp. 73–78.
By T. Jousimaa, "Fluff Pulps—Their Characteristics and Application", The Pira Fibramerics Programme, vol. 1, Nov. 1989, pp. 1–10.

*Primary Examiner*—John G. Weiss
*Assistant Examiner*—Dennis Ruhl
*Attorney, Agent, or Firm*—Young & Thompson

[57] ABSTRACT

The present invention relates to an absorbent body which is intended to form the absorbent element in an absorbent article, such as a diaper, an incontinence guard or a sanitary napkin, and includes a first absorbent layer which, in use, is intended to face towards the wearer, and a second absorbent layer which is intended, in use, to face away from the wearer. According to the invention, the absorbent body includes at least two mutually different cellulose fluffs, wherein the major part of the fibre structure of the first absorbent layer is comprised of a first type of cellulose fluff having low liquid-spreading ability and a critical bulk which exceeds 8 cm³/g at 2.5 kPa, while the major part of the fibre structure of the second absorbent layer is comprised of a different type of cellulose fluff having a critical bulk beneath 8 cm³/g at 2.5 kPa and a higher liquid-spreading ability than the cellulose fluff in the first absorbent layer. The second absorbent layer will therefore be highly capable of draining liquid from the first absorbent layer. The second absorbent layer includes superabsorbent material which is admixed generally uniformly in the cellulose fluff within at least one area of the layer.

14 Claims, 10 Drawing Sheets

U.S. PATENT DOCUMENTS

| | | |
|---|---|---|
| 4,047,531 | 9/1977 | Karami . |
| 4,699,619 | 10/1987 | Bernardin . |
| 4,798,603 | 1/1989 | Meyer et al. . |
| 4,818,315 | 4/1989 | Hellgren et al. . |
| 4,898,642 | 2/1990 | Moore et al. . |
| 5,019,063 | 5/1991 | Marsan et al. . |
| 5,741,241 | 4/1998 | Guidotti et al. ............ 604/368 |

FOREIGN PATENT DOCUMENTS

| | | |
|---|---|---|
| 0 399 564 | 11/1990 | European Pat. Off. . |
| 0 401 189 | 12/1990 | European Pat. Off. . |
| 0 440 472 | 8/1991 | European Pat. Off. . |
| WO90/00041 | 1/1990 | WIPO . |
| WO 91/11163 | 8/1991 | WIPO . |
| WO 91/11165 | 8/1991 | WIPO . |

ABSORBENT BODY FOR ABSORBENT ARTICLES

CROSS REFERENCES TO RELATED APPLICATIONS

This is a continuation-in-part of co-pending prior application Ser. No. 08/674,490 filed Jun. 28, 1996, which is a file wrapper continuation of Ser. No. 08/256,190 filed Jun. 28, 1994, both now abandoned which is a 371 of PCT/SE92/00078 Feb. 10, 1992.

FIELD OF THE INVENTION

The present invention relates to an absorbent body which is intended to form the absorbent element of an absorbent product, such as a diaper, an incontinence guard or a sanitary napkin, and which comprises a first absorbent layer, which is intended to face towards the skin of the wearer, and a second absorbent layer which is remote from the wearer in use; and also to an absorbent article which includes such an absorbent body.

BACKGROUND OF THE INVENTION

An absorbent body, or absorbent pad, for use with absorbent articles, such as disposable diapers, sanitary napkins and incontinence guards, is normally comprised of one or more layers of cellulose fluff, and will more often than not include so-called superabsorbents, which are polymers capable of absorbing several times their own weight of water or body liquid. The absorbent body may also include other constituents, for instance constituents which will improve the liquid-spreading properties of the absorbent body, or constituents which will enhance the ability the absorbent body to hold together and to resist deformation during use.

One serious problem with present-day absorbent articles, and primarily in the case of diapers and incontinence guards which are intended to receive and absorb relatively large quantities of liquid, is that the articles often leak long before their total absorption capacity has been fully utilized. One reason for this leakage is that those absorbent bodies known hitherto are unable to rapidly take-up and absorb large liquid quantities effectively.

Although an absorbent body which includes superabsorbents has a high absorption capacity and is able to retain the liquid absorbed, even when the absorbent body is subjected to external pressure, the superabsorbents have an extremely low absorption rate. Since urination often involves the discharge of large quantities of liquid over a period of some few seconds, the absorbent body will often become saturated with liquid temporarily, so that any further liquid that is discharged will flow out of the absorbent body.

This premature leakage is naturally very irritating to the person concerned, or to the person nursing the afflicted person. The fact that they may not be able to rely on the proof of an incontinence guard against leakage is a constant worry to adult incontinents who are otherwise healthy people and who depend on an effective guard in order to be able to enjoy a normal working and social life. Furthermore, premature leakage of children's diapers and adult diapers and incontinence guards means that wet clothes and bed linens must be changed and washed more often than would otherwise be necessary.

Great efforts have been made in the past to produce an absorbent body which is capable of rapidly absorbing large quantities of liquid. For example, U.S. Pat. No. 3,441,023, U.S. Pat. No. 4,276,338, EP 124 365, U.S. Pat. No. 4,333, 462, EP 343 940 and EP 343 941 propose that cavities or basin-like hollows are formed in the absorbent body.

Serious endeavours have also been made in attempts to control the flow of liquid in the absorbent body, by compressing different layers or regions of said body to different high degrees or in different patterns. Variations in the degrees of compression also varies the capillary structure of the absorbent body and therewith also its liquid transporting ability. Since liquid is always transported from the coarser to the finer capillaries, liquid will be transported in such structure from the regions of low degrees of compression to regions of high degrees of compression. It is difficult, however, to create density differences which are sustained both in a wet and a dry state, simply by compression, since cellulose fluff tends to assume its critical bulk when wet. Critical bulk is the bulk at which a given cellulose fluff body will neither collapse nor expand when wetted. This means that a cellulose fluff body which has been compressed to a bulk beneath its critical bulk will swell when wetted, whereas a body whose bulk is higher than the critical bulk will collapse when wetted.

SE 458 418 describes an absorbent body which has a density gradient that has been made wet-stable with the aid of a heat meltable binder. One drawback with an absorbent body of this kind is that the binder impairs the absorbency of the body. Another drawback is that the binder is relatively expensive and therewith increases the cost of the finished absorbent body, which is particularly unsuitable in the case of absorbent bodies which are intended for one-time-use only.

In order to increase the ability of an absorbent body to absorb a large quantity of liquid over a short period of time, it is proposed in EP 0 325 416 that a low density region is provided in that part of an absorbent body which is intended to face forwards on a wearer in use. The intention with this particular arrangement is that discharged body liquid can be quickly taken-up in the relatively coarse capillaries in the region of low density and then be absorbed by the surrounding material of high density. Because of the differences in the size of the capillaries between the liquid-receiving region and the surrounding material the liquid-receiving region will be emptied of liquid to a significant extent before liquid is next delivered to the absorbent body.

One serious drawback with an absorbent body according to EP 0 325 416, however, is that it is difficult to maintain the low density in the liquid-receiving region when the body is in use, particularly when the absorbent body is comprised of cellulose fluff. When the absorbent body is used in a diaper for instance, the liquid-receiving region is located in the user's crotch and there subjected to strong mechanical influences by the movements of the wearer's legs or thighs. Consequently, the absorbent pad becomes deformed and is compressed together or pleated into string or sausage-like shape. The liquid-receiving region therewith loses its shape and can be more or less rendered totally ineffective during use. Such deformation is particularly noticeable in a wet absorbent body which is made of cellulose fluff. Such an absorbent body can therefore only be wetted once, before the risk of leakage becomes serious.

Another problem with absorbent articles is one of keeping the surface that faces towards the wearer in use as dry as possible during the whole period of use and to prevent so-called re-wetting. Re-wetting occurs when absorbed liquid is pressed out of the absorbent body and wets the skin of the wearer. This is prevented to some extent when the absorbent body contains superabsorbents, which chemically bind the absorbed liquid even when the article is subjected to external pressures, for instance when the wearer sits down. One difficulty, however, is that of constructing the absorbent body in a manner such that the liquid will spread within the body and reach the superabsorbent material.

U.S. Pat. No. 4,047,531 describes an absorbent article whose absorbent body includes a first layer which is comprised of mechanical fluff thermomechanical fluff or semichemical fluff, and a second layer which is comprised of a material different to that of the first layer and consists of thermomechanical fluff, semichemical fluff or chemical fluff. The materials in the two layers are chosen so that the fibres in the first layer are more hydrophobic than the fibres in the second layer.

In a first embodiment, the first layer is comprised of thermomechanical fluff, while the second layer is comprised of chemical fluff. By using thermomechanical fluff in the first layer, there is obtained a higher yield of the wood raw material and it is said that such fluff is more environmentally friendly in manufacture than chemical fluff. It is also said that less energy is required to defibre sheets of thermomechanical fluff. The risk of re-wetting is also reduced with the use of two different fluffs.

Chemical fluff will collapse when wet and therewith obtain a dense structure of good liquid-spreading ability but of low liquid retention. An absorbent body which is comprised solely of chemical pulp will result in a high degree of re-wetting when subjected to pressure. On the other hand, thermomechanical fluff is highly resilient or springy when wet, and therewith is more able to resist compression. Because the materials in the two layers have different degrees of hydrophobicity, absorbed body liquid is transported from the more hydrophobic layer to the layer which is less hydrophobic. It is said that the risk of re-wetting is minimized in this way.

U.S. Pat. No. 4,047,531 uses the terms "mechanical", "thermomechanical", "semimechanical" and "chemical" to characterize different types of cellulose fluff. These terms, however, are not sufficiently defined to disclose clearly those properties that are required of the fluffs in order for the resultant absorbent body to obtain the properties stated. The terms used merely indicate the properties that can be expected of the fluffs with a starting point from the stated methods of manufacture. It is possible, however, to subsequently treat the fluffs in different ways and thereby change their hydrophobicities for instance, such as to completely reverse the order of hydrophobicity disclosed in U.S. Pat. No. 4,047,531.

Furthermore, the degree of hydrophobicity is only one of several parameters which control the transport of liquid in a fibre structure. Equally as important parameters include, for instance, the porosity of the structure and the relationship between the sizes of the capillaries in the body layers. A dense, relatively hydrophobic structure may thus have greater ability to spread liquid than a porous, less hydrophobic structure.

In order to be able to receive large quantities of liquid over a short period of time, an absorbent body will preferably have an open fibre structure which will accommodate a large quantity of liquid between its fibres. In this case, the hydrophobicity of the fibre structure is of less importance, provided that the liquid is able to penetrate into the absorbent body.

SUMMARY OF THE INVENTION

The present invention, however, provides an absorbent body of the kind mentioned in the introduction which has a high instantaneous liquid-absorption capacity and which is able to counteract re-wetting of the wearer's skin by the liquid absorbed in the body.

An inventive absorbent body is primarily characterized in that the body includes at least two mutually different fluffs, wherein the fibre structure in the first absorbent layer is comprised generally of a first type of fluff having a low liquid-spreading ability and a critical bulk exceeding 8 $cm^3/g$ at 2.5 kPa, and wherein a major part of the fibre structure of the second absorbent layer is comprised of another type of fluff having a critical bulk beneath 8 $cm^3/g$ at 2.5 kPa and having a higher liquid-spreading ability than the fluff in the first absorbent layer, whereby the second absorbent layer has a greater ability to drain liquid from the first absorbent layer; and in that the second absorbent layer includes superabsorbent material which is admixed generally uniformly in the fluff within at least one region of the second layer.

Preferably the the second absorbent layer is comprised of fluff having a critical bulk of at most 7 $cm^3/g$ at 2.5 kPa, especially at most 6 $cm^3/g$ at 2.5 kPa.

When two different types of cellulose fluffs having mutually different absorption characteristics are combined in the manner proposed in accordance with the invention, there is obtained an absorbent body whose properties are impossible to obtain with the use of one single type of fluff alone.

The absorption properties of a cellulose fluff are, to some extent, determined by the manner in which the pulp has been produced.

When producing cellulose fluff chemithermomechanically, the yield is more than 90% of the starting material, in this case wood chips. The chemithermomechanical process is begun with an impregnating step, in which the active chemicals act on the wood chips at elevated temperatures. The chemically saturated chips are then refined to form free fibres. The resultant pulp is then screened, washed and bleached with peroxide. This bleaching does not affect the process yield, but leaves in the pulp lignin in a concentration of about 27%, together with resins and hemicellulose.

Chemical cellulose fluff is produced by impregnating wood chips and then cooking the chips so that lignin and readily-dissolved cellulose pass into the cooking liquor. The yield obtained from the wood chips in this process is much lower an the yield obtained with mechanical and chemimechanical pulps, and lies around 50%. Upon completion of the cooking process, the pulp is screened and washed prior to being bleached with chlorine chemicals, therewith lowering the yield still further. For example, such pulp will contain practically no lignin.

Compared with chemically produced cellulose fluff a chemithermomechanically produced cellulose fluff will generally have a greater pore volume, higher wet stability and low liquid-spreading ability. Because the cellulose fluff has a large pore volume, the capillaries between the fibres will be coarse, which is one reason, of course, why such fluff has a low liquid-spreading ability, since this ability decreases with increasing capillary sizes. The liquid-spreading ability of the cellulose fluffs and their affinity to liquid also depends on that residual wood substances impart to the fibres of chemithermomechanical pulps other surface properties than the fibres of chemical pulps.

One reason for the high wet stability of chemithermomechanical fluffs is their relatively coarse fibres, having a fibre weight of between 180–600 mg/km. The fluff also contains lignin, which acts as a fibre-stiffening element. Since lignin retains its structure even when wet, fibres which have a relatively high lignin content are relatively rigid even in a wet state. Consequently, a fibre layer which is comprised substantially of such fibres will have good wet stability. A cellulose fluff which possesses good wet stability will also have an open structure in a wet state, with coarse capillaries and a small number of fibres per unit of volume. This means that a cellulose fluff of this nature will have a comparatively high absorbency, since a major part of the liquid absorbed by the cellulose fluff structure takes place in the spaces between the fibres, while only a minor part of the liquid is absorbed in the actual fibres themselves.

Cellulose fluff which has a low liquid-spreading ability does not function as well when used together with superabsorbents, when the intention is to utilize the absorbency of the superabsorbents to the greatest possible extent. This is mainly because only those superabsorbents which are in direct contact with the primary wet region of the absorbent body can be utilized. It is meaningless, however, to conglomerate a large quantity of superabsorbents within the region of the absorbent body where wetting takes place. The superabsorbents, which are normally present in the form of particles, such as powder, flakes, fibres or granules, swell when absorbing liquid, to form a gel. In this respect, there is a risk that the superabsorbent particles will form a more or less continuous gel which functions as a liquid barrier and prevents absorption of further deliveries of body liquid to the absorbent body. Absorption occurs within the superabsorbent particles as a result of diffusion, which is a very slow process. In practice, the aforesaid continuous gel is thus impermeable to liquid.

Chemically produced cellulose fluff, on the other hand, generally has a good liquid-spreading ability and is thus suitable for use together with superabsorbents. Since chemical cellulose fluffs are generally comprised of pure cellulose, they have fine fibres with a weight of 140–190 mg and low stiffness and low wet stability. A fibre structure which is comprised substantially of chemically produced cellulose fluff will have a large number of fibres per unit of volume, which results in a dense structure that possesses fine capillaries. When a fibre structure of this nature is wetted, it will collapse due to the low wet rigidity of the fibres, so as to form a structure of relatively low absorbency but of high liquid-spreading ability.

When using an inventive absorbent body, discharged body liquid, or body fluid, will first be deposited on and penetrate into the first fluff layer located nearest the wearer's skin. This layer has a low liquid-spreading ability, but has an open structure which presents a low resistance to flow and which is able to take-up a relatively large quantity of liquid in a short period of time. When seen in the direction from the wearer, there is arranged outwardly of this layer a second fluff layer which has a high liquid-spreading ability. In order to provide the absorbent body with a sufficient absorption capacity and to enable the body to retain absorbed liquid as far away from the wearer's body as possible, the second fluff layer contains superabsorbent material in addition to cellulose fluff. As before mentioned, superabsorbent material has a low absorption rate and has practically no intrinsic liquid-spreading ability. It is therefore very essential that the fibre material surrounding the superabsorbent material is able to disperse the liquid throughout the absorbent layer, so that said liquid will reach as much of the absorbent material as possible. This liquid is gradually absorbed from the pores or capillaries of the fibre structure to the superabsorbent material and there bound in gel form.

Liquid is taken-up more slowly in the second fluff layer than in the first fluff layer, since the fibre structure has finer capillaries and since the space between the fibres available for immediate absorption is small. However, the absorbed liquid is transported gradually away from the area originally wetted and is spread between the fibres and out into the fibre layer through the action of capillary forces, where it is absorbed by the superabsorbent material. This spreading of the liquid through capillary action, however, is comparatively slow. Consequently, the body liquid discharged will be collected in the first layer of cellulose fluff located nearest the wearer, this layer also functioning as a buffer, or reservoir, which is emptied progressively in time with the absorption and spreading of liquid in the second fluff layer distal from the wearer. It is essential to the present invention that a difference in capillary size exists between the two fluff layers and that the second fluff layer has smaller capillaries than the first fluff layer. This results in an active transportation of liquid from the first layer to the second layer, since the capillary forces will always act for the transportation of liquid from coarser to finer capillaries. This difference in capillary sizes also counteracts re-wetting of the wearer by liquid which has already been absorbed in the second absorbent layer.

The first fluff layer is comprised mainly of cellulose fluff having a high critical bulk, suitably a bulk which exceeds 8 $cm^3/g$ at 2.5 kPa, whereas the second fluff layer is comprised mainly of cellulose fluff having a low critical bulk, suitably a bulk beneath 8 $cm^3/g$ at 2.5 kPa. A cellulose fluff of high critical bulk will have an open structure with a large pore volume even when wet As before mentioned, the critical bulk is the bulk at which a cellulose pulp body will neither collapse nor expand when wetted. Because the two fluff layers have mutually different critical bulks, they will also have mutually different pore volumes when wet.

Another contributory factor to the low re-wetting and high surface dryness of an inventive absorbent body is that the liquid present in the first layer is not spread out in said layer but remains in the region nearest the so-called wetting point, i.e. the point at which the liquid first enters the absorbent body. This greatly limits the moist surface area that can come into contact with the wearer's skin.

Since the second fluff layer gradually absorbs liquid from the first fluff layer, the first fluff layer will be practically emptied of the liquid that is absorbed in the spaces between adjacent fibres. In this way, the first layer is again able to receive and to absorb a large quantity of rapidly discharged liquid, without risk of the fibre structure becoming saturated. In the case of diapers, sanitary napkins and incontinence guards, the discharge of liquid or fluid takes place during short periods of time that are interspersed with periods where no liquid is discharged, as distinct from a continuous flow of liquid or fluid. Thus, there is time for the first absorbent layer to be essentially emptied of liquid between the occasions when liquid is discharged, so that available absorption capacity is always found when a further quantity of liquid, or fluid, is discharged.

It is appropriate for the first absorption layer to also include at least a minor quantity of superabsorbent material. This is because a small quantity of liquid will always remain between the fibres in the first fluff layer and may cause rewetting or cause the absorbent body to be felt to be moist. The superabsorbent material however, will absorb and bind this residual moisture. Thus, there is obtained in this way an absorbent article in which the surface of the absorbent body facing the wearer's skin will be extremely dry and comfortable, even though the article may have absorbed considerable quantities of liquid.

It is also appropriate to choose for the first absorbent layer a superabsorbent material which has a relatively low absorption rate. This will enable essentially all body liquid or fluid discharged into the first layer to be transported to the second absorption layer before the superabsorbent material begins to absorb the small quantity of liquid that remains in the first absorption layer.

DETAILED DESCRIPTION OF THE INVENTION

The invention will now be described in more detail with reference to a number of working embodiments.

The ability of an absorbent layer to drain liquid from another absorbent layer is determined in accordance with the following method:

Method 1

Two rectangular cellulose fluff bodies measuring 10×28 cm are prepared. These bodies are referred to as K1 and K2 respectively in the following.

The test bodies K1 and K2 were weighed and their weights per unit area determined. K2 was then placed on a plexiglass plate and covered with a net, whereafter K1 was placed on top of K2 and the net. The combined test body, consisting of K1 and K2, was compressed to a bulk of 7 cm³/g. 60 ml of a 0.9 percent by weight NaCl-solution was then added to K1 and the combined sample body was placed under a load of 0.5 kPa (1.4 kg). After 20 minutes, K1 was weighed and then placed again on top of K2. This procedure, including the addition of liquid and weighing, was repeated a further three times. K1 and K2 were then subjected to a load of 2.5 kPa (7.0 kg) for 5 minutes, whereafter K1 was again weighted.

The amount of liquid remaining in K1 was determined after each weighing step as $$\frac{Kl_v - Kl_t}{Kl_t} \text{ [g liquid/ g cellulose full body]}$$

where $Kl_t$=the dry weight of K1

$Kl_v$=the wet weight of K1

EXAMPLE 1

Six samples a–f were prepared, each comprising a top fluff layer K1 and a bottom fluff layer K2. Both K1 and K2 had a weight per unit area of 550 g/m² and each contained 3.0 g of superabsorbent, which was mixed generally homogeneously with the fluff fibres.

K1 and K2 had the following fluff composition in the various tests:

TABLE 1

| Test | K1 | K2 |
|------|------|------|
| a | 100% F1 | 100% F2 |
| b | 100% F1 | 80% F2, 20% F1 |
| c | 100% F1 | 60% F2, 40% F1 |
| d | 100% F2 | 100% F2 |
| e | 100% F1 | 100% F1 |
| f | 100% F2 | 100% F1 | where F1 was OCTMP 146 from Ostrand and F2 was Vigor fluff EA from Korsnäs. In those layers which contained both fluffs, the fluffs were present as a generally homogenous mixture. The ability of K2 to drain liquid from K1 was determined in accordance with Method 1 and the amount of liquid which remained in K1 after the aforesaid different time intervals was plotted in the diagram of FIG. 3. The measured values are the mean values of two measuring processes.

F1 is a cellulose fluff having a critical bulk in excess of 8 cm³/g at 2.5 kPa, a relatively high resiliency even when wet, a large pore volume and a low liquid-spreading ability.

F2 is a cellulose fluff which has a critical bulk beneath 8 cm³/g at 2.5 kPa, a low wet resiliency, a small pore volume and a high liquid-spreading ability.

Figure 3:
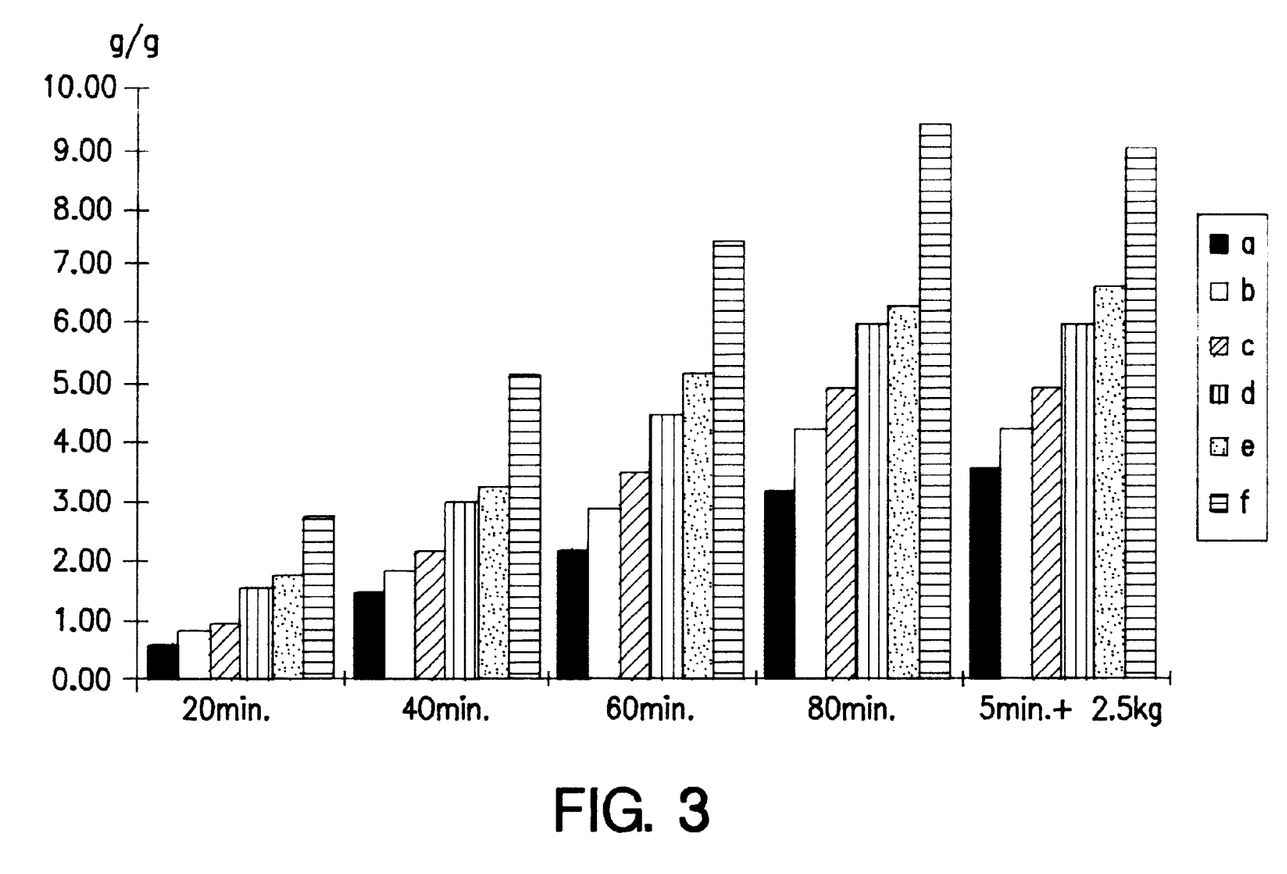
FIG. 3 is a diagram representing the amount of liquid remaining in a top fluff layer of six different samples at different time intervals.

As can be seen from the diagram of FIG. 3, the drainage of K1 is between three and four times more effective in test a than in test f. This means that it is much more advantageous to place a layer having the properties described for F1 over a layer having the properties described for F2, than vice versa.

Also when test a is compared with tests d and a, in which the two layers K1 and K2 are comprised of the same kind of fluff, it will also be seen that test a has a surprisingly superior drainage value.

The drainage value obtained at the higher load, this value being essentially the same as the drainage value obtained after the last liquid addition, shows that the drainage properties are essentially unaffected by externally applied pressure, and that substantially no re-wetting takes place from K2 to K1.

A further test was carried out with the intention of investigating the liquid-spreading abilities of a number of absorbent bodies.

Method 2

A rectangular test body measuring 10×28 cm was punched out. A line was drawn across the sample body 10 cm from the short side of the test body.

A liquid container measuring 250 mm×250 mm×42 mm was placed adjacent laboratory scales having a measuring accuracy of 0.1 g, and both the scales and the liquid container were adjusted to a horizontal position. A plexiglass plate was placed on the scales at an angle of 30°, with one free edge of the plate extending down slightly into the container. A 0.9 percent by weight NaCl-solution was then poured into the container, so that 10 mm of the inclined plexiglass plate was located beneath the surface of the liquid.

The test body was then weighed and its weight was noted to an accuracy of 0.1 g.

The scales were tared and the test body was placed on the inclined plexiglass plate with the marking on the test body located at a distance of 10 cm from the submerged edge of the plexiglass plate, while the edge of the test body directed towards the liquid was held raised so as to prevent contact of said edge with the liquid. This edge of the test body was then released into the liquid, while initiating a time-take at the same time. A reading of the scales with the plexiglass plate and test body was made every minute, and the weight noted. The liquid level of the container was held constant during the measuring process, with the aid of a circulation pump. The measuring processes were stopped after a period of 10 minutes.

The liquid-spreading ability of the test body was determined as $$\frac{m_2}{m_1} \ [g/g],$$

where $m_1$=the weight of the test body when dry $m_2$=the weight of the liquid absorbed Each calculation was made with values corresponding to the mean values of two measuring processes.

EXAMPLE 2

The liquid-spreading abilities of the three different cellulose fluffs were determined in accordance with Method 2.

The cellulose fluffs were

KEA=Vigor fluff EA from Korsnas AB

SEC=STORA EC from STORA CELL

Ö=ÖCTMP 146 from SCA Wifsta-Östrand AB

The test bodies had a bulk of 10 cm$^3$/g.

Figure 4:
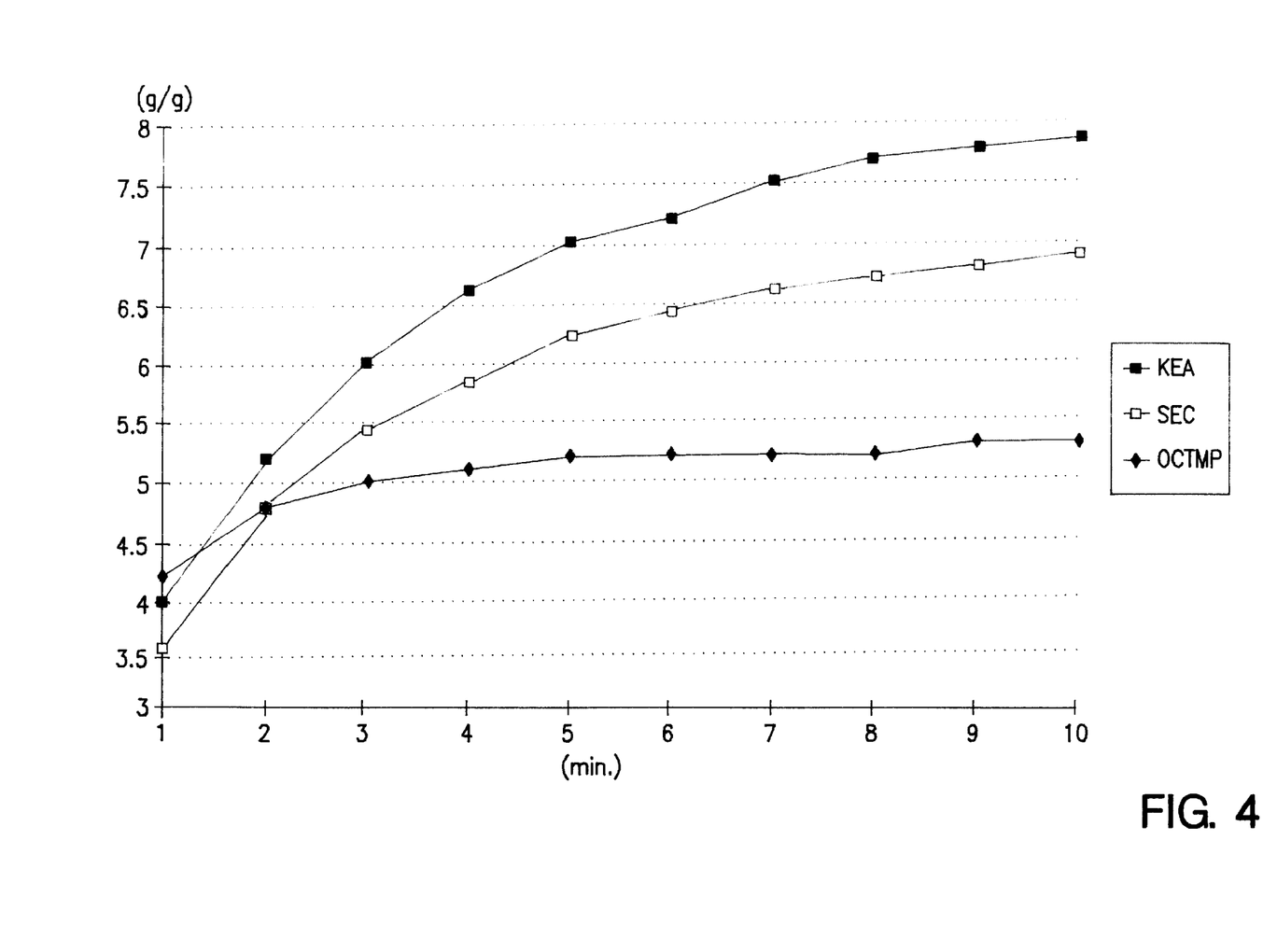
FIG. 4 is a diagram representing the liquid-spreading abilities of three different cellulose fluffs.

The results of the measurements are plotted in the diagram of FIG. 4, from which it will be seen that the chemically produced cellulose fluffs KEA and SEC have a higher liquid-spreading ability than the chemithermomechanically produced fluff Ö.

EXAMPLE 3

The liquid-spreading abilities of a further four mutually different fluffs were determined in the same manner as that described in Example 2. The cellulose fluff were Ö=ÖCTMP 146 from SCA Wifsta-Östrand AB CTMP 70=CTMP 70 from STORA CELL SPHINX=SPHINX from Metsä-Serla KEA=Vigor fluff EA from Korsnäs AB The test bodies also had a bulk of 10 cm$^3$/g in this test.

Figure 5:
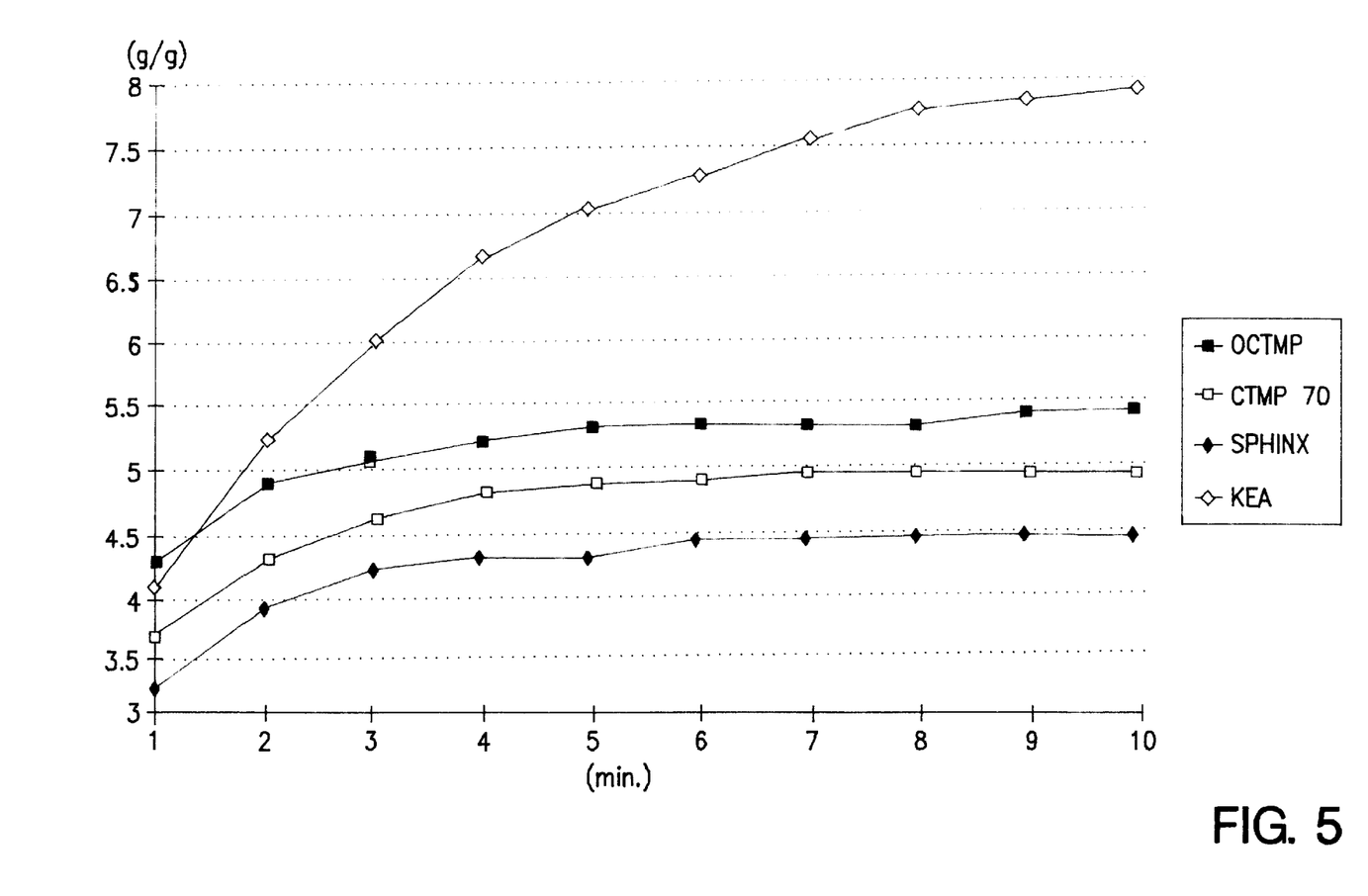
FIG. 5 is a diagram representing the liquid-spreading abilities of four different fluffs.

The results are plotted in the diagram of FIG. 5 and show that the chemithermo-mechanically produced fluffs, i.e. all fluffs with the exception of KEA, have a considerably lower liquid-spreading ability than the chemically produced fluff.

EXAMPLE 4

The spreading ability of three test bodies, a–c having a bulk of 7 cm$^3$/g was determined in accordance with Method 2, although in this case the measuring processes were continued for 60 minutes and the weights of respective test bodies were noted at 10-minute intervals. The test bodies comprised a top layer having a weight per unit area of 400 g/m$^2$ and a bottom layer having a weight per unit area of 700 g/m$^2$. Each test body contained 6.0 g superabsorbent which was distributed uniformly in the body, such that the top layer contained 2.2 g superabsorbent and the bottom layer contained 3.8 g superabsorbent. The superabsorbents used were SANWET IM 2200 D from Sanyo Chemical Industries Ltd.

The various test bodies had the following fluff composition:

TABLE 2

| Test | Top Layer | Bottom Layer |
|---|---|---|
| a | 100% F1 | 60% F2, 40% F1 |
| b | 100% F1 | 80% F2, 20% F1 |
| c | 100% F1 | 100% F2 |

Similar to Example 1, F1 was OCTMP 146 from Östrand and F2 was Vigor fluff EA from Korsnäs.

Figure 6:
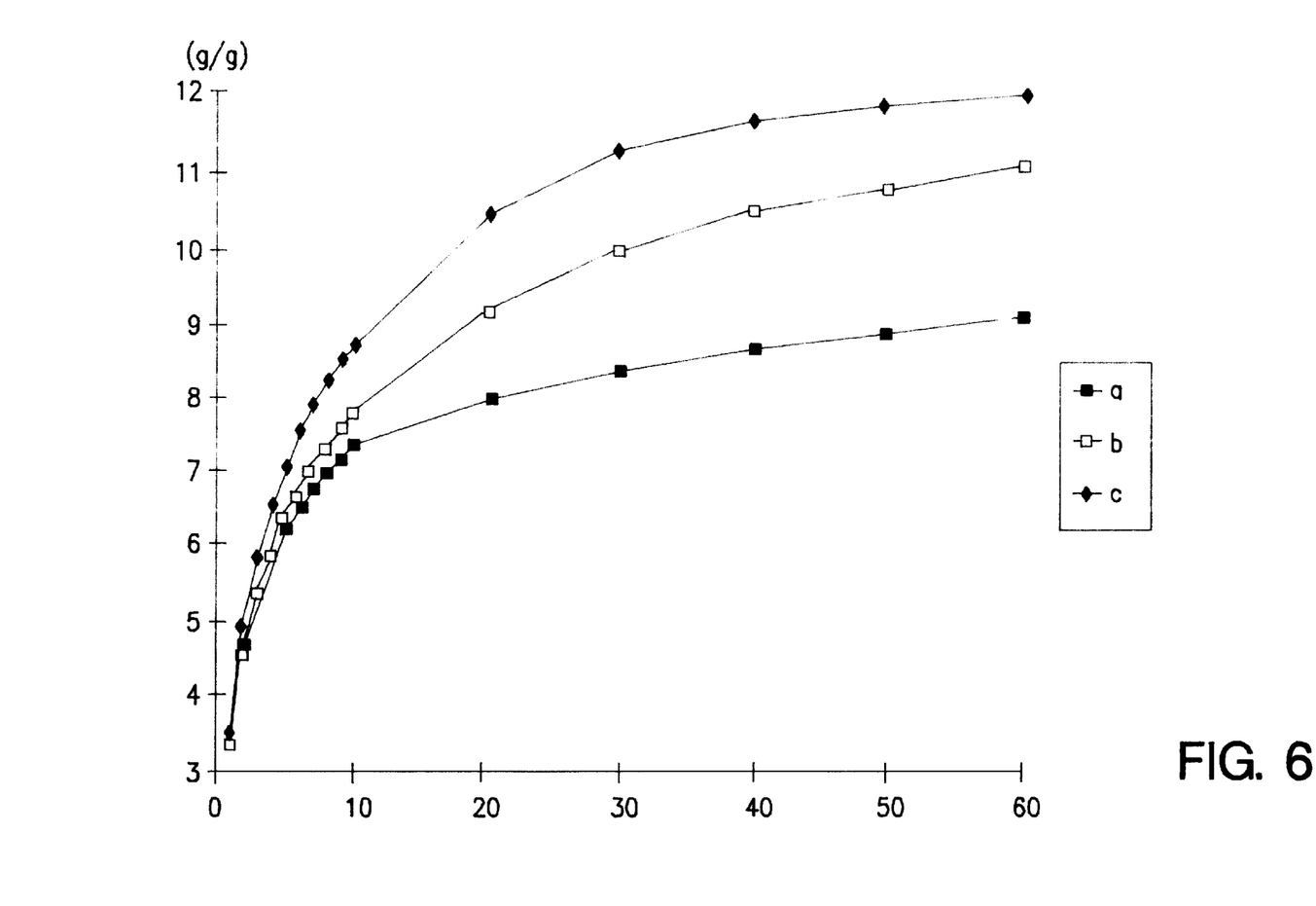
FIG. 6 is a diagram representing the liquid-spreading abilities of three test bodies having different bottom layers.

The liquid-spreading abilities of the test bodies have been plotted in the diagram of FIG. 6 in g/g on each weight reading occasion. It will be seen from the diagram of FIG. 6 that the liquid-spreading ability increases with increasing concentrations of F2 in the bottom absorbent layer, which is only to be expected since F2 is a cellulose fluff that possesses a high liquid-spreading ability, as earlier mentioned.

At the end of the measuring time, each test body was divided transversely into five pieces of equal size. These were numbered from 1 to 5 in a rising number order beginning from the piece which, during the measuring process, was located closest to the liquid, and ending at the piece which was located furthest away from the liquid during said process. The total weight of each piece was determined and the results plotted in the diagram of FIG. 7. This diagram also shows that the ability to spread liquid increases with increasing admixture of F2 in the bottom absorbent layer, since the test-body piece 5 located furthest from the liquid has the highest weight for the test body c.

EXAMPLE 5

A further series of measurements were carried out on test pieces d-f. Measurement was effected in the same manner as that described in Example 2. The test bodies consisted of two layers, both of which had a weight per unit area of 550 g/m$^2$. As in the case of Example 4, 6.0 g superabsorbent was distributed evenly in the absorbent body, with 3.0 g in each layer. The superabsorbent and the cellulose fluff used and also their mutual mixing ratios were the same as those in Example 4.

Figure 7:
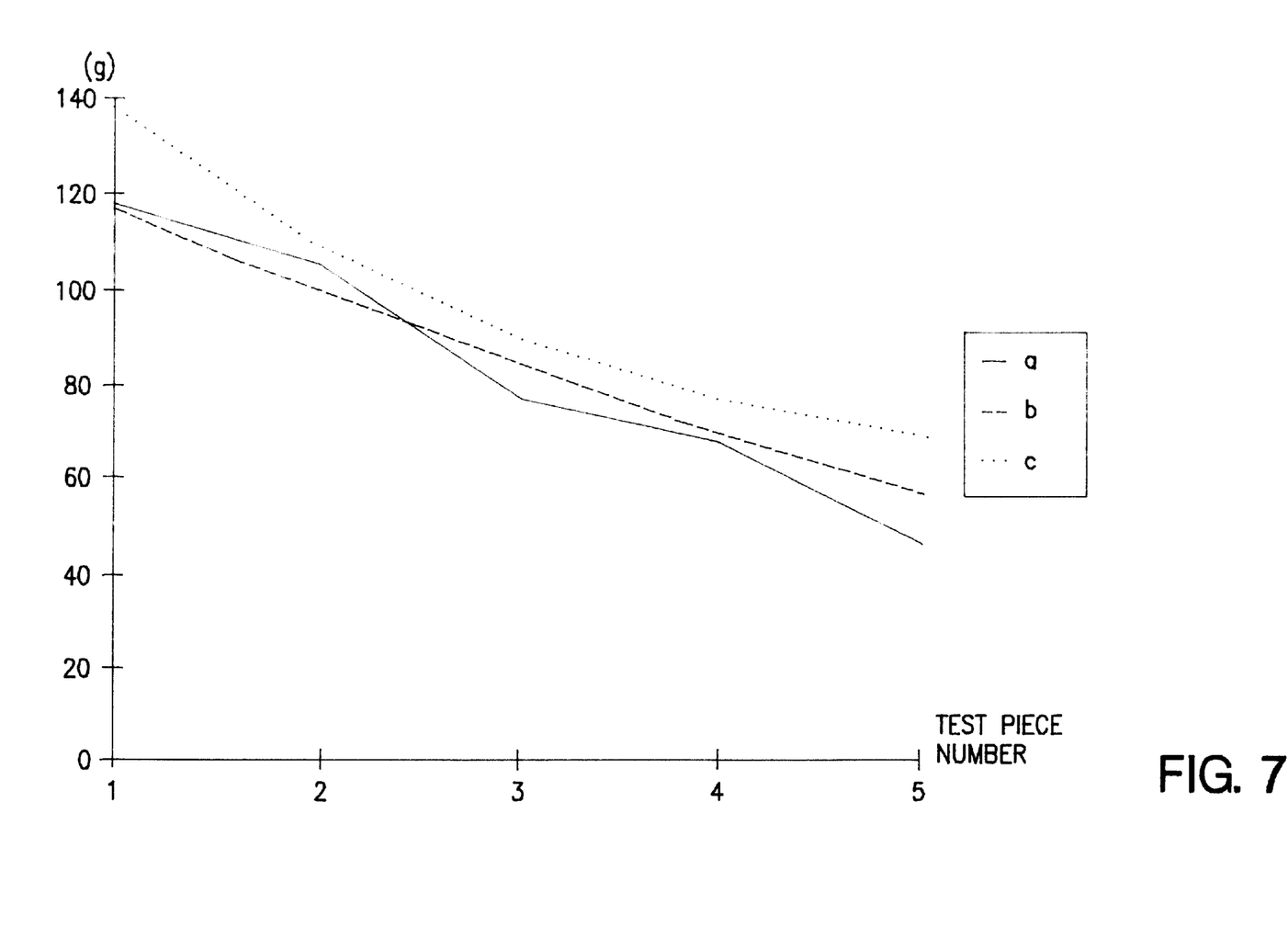
FIG. 7 is a diagram representing the total weight of each of five pieces obtained by subdividing three test bodies.
Figure 8:
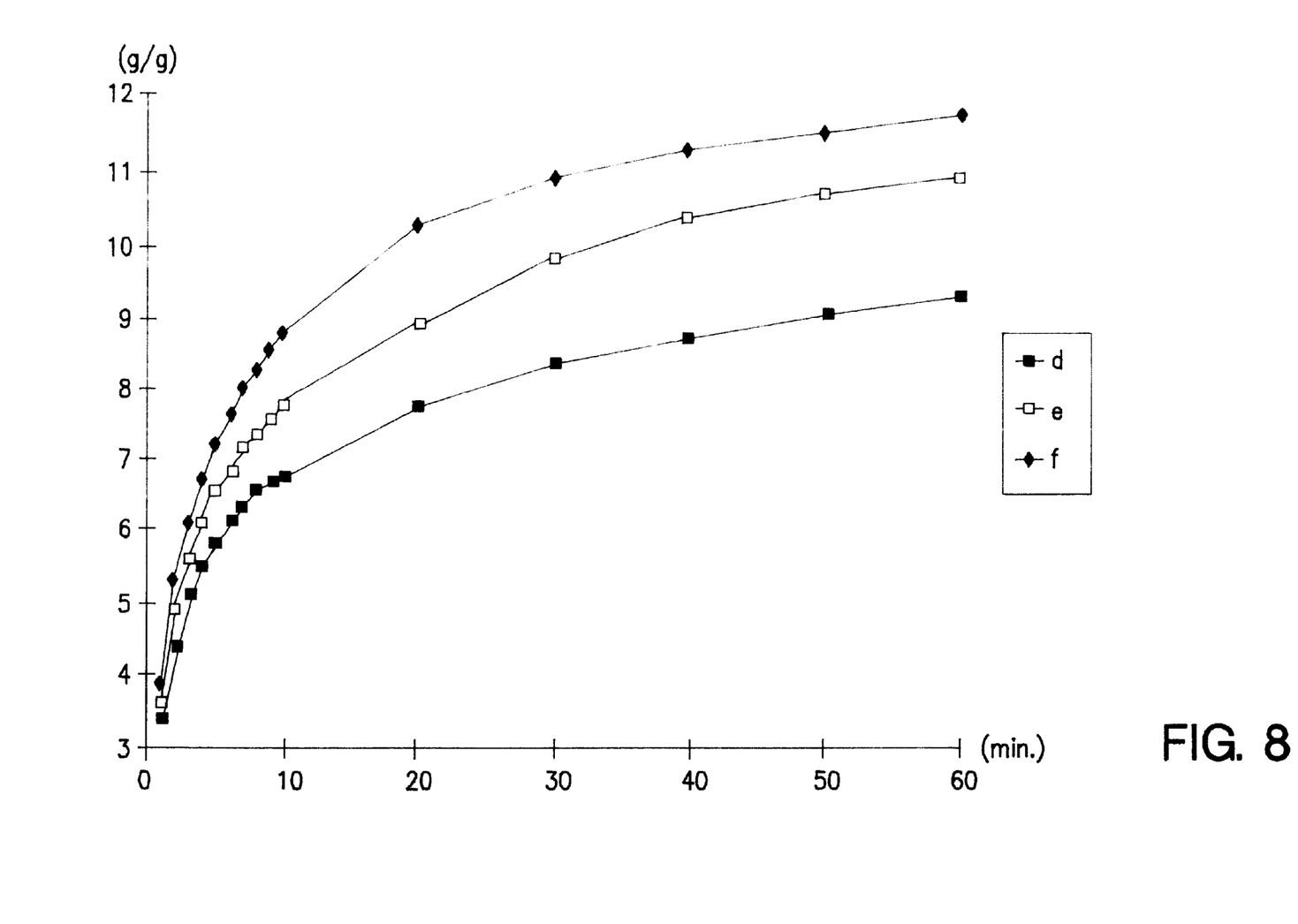
FIG. 8 is a diagram representing the liquid-spreading abilities of three test bodies having different bottom layers.
Figure 9:
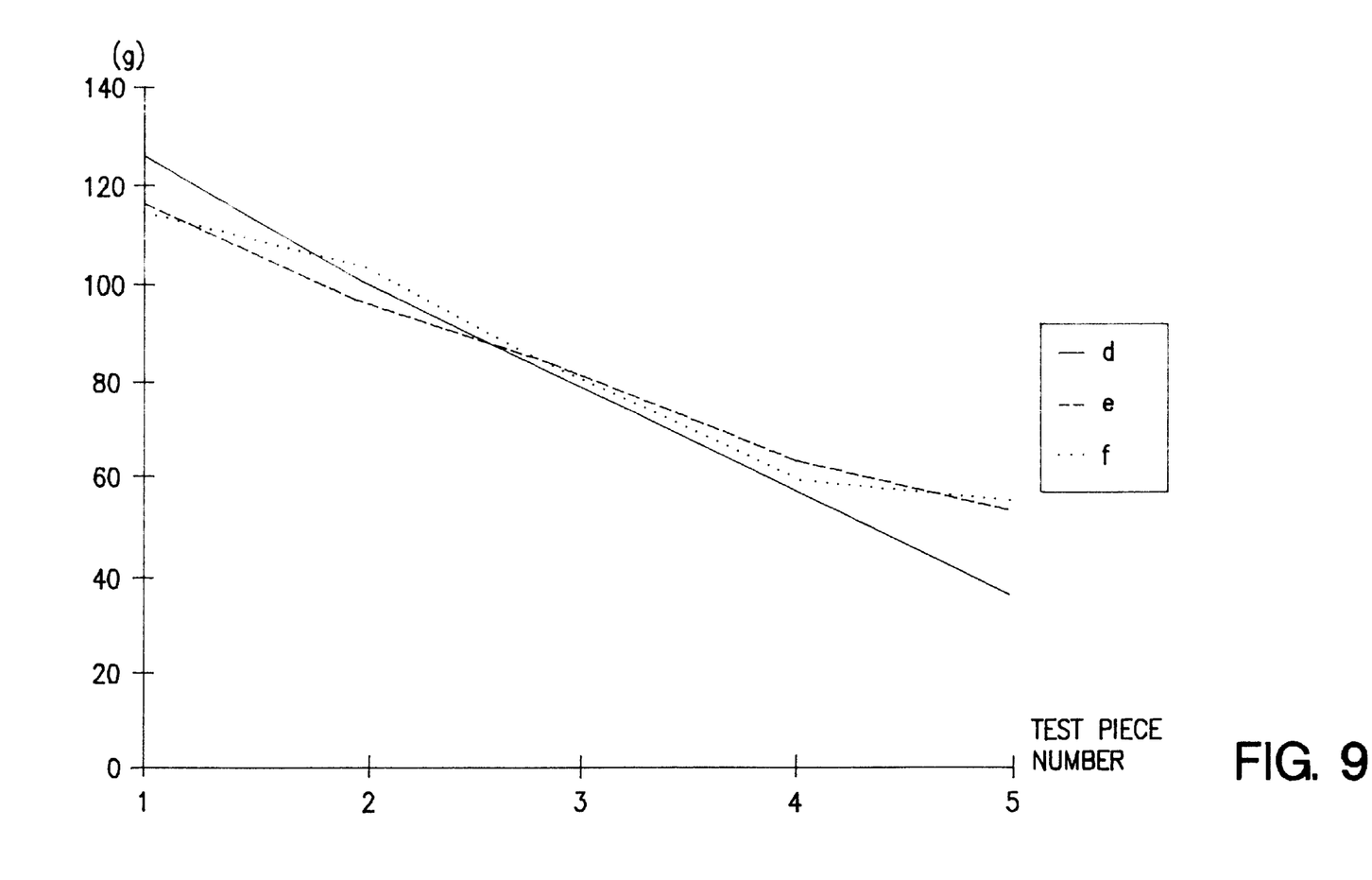
FIG. 9 is a diagram representing the total weight of each of five pieces obtained by subdividing three test bodies.

The measuring results were plotted in the diagrams of FIGS. 8 and 9 and show, similar to the diagrams of FIGS. 6 and 7, that the liquid-spreading abilities of the test bodies increase with an increasing admixture of cellulose fluff with high liquid-spreading ability in the bottom absorbent layer.

EXAMPLE 6

Further tests 1–5 were performed with pulps having critical bulks between 5.5 and 8.5 cm$^3$/g.

In accordance with Method 1, the remaining liquid in the upper core at repeated wettings was measured as ability of the lower core to drain the upper core.

The absorption speed was measured as the acquisition time at repeated wettings by four additions of each 75 ml synthetic urine at 20 minutes intervals. The time measured was the time when all liquid had been absorbed according to visual inspection.

The test bodies measured 10×28 cm and consisted in all cases of an upper core and a lower core with a density of about 0.17 g/cm$^3$. The upper core had a weight per unit area of 400 g/m$^3$ and contained an admixture of 10% superabsorbent material. The lower core had a weight per unit area of 700 g/m$^3$ and contained an admire of 20% superabsorbent material. The lower core consisted of chemical cellulose fluff having a critical bulk of about 6 cm$^3$/g and the upper core consisted of cellulose fluffs having critical bulks between about 5.5 and 8.5 cm$^3$/g. The test results are shown in the following Tables 3 and 4 and in the diagrams of FIGS. 10 and 11.

Figure 10:
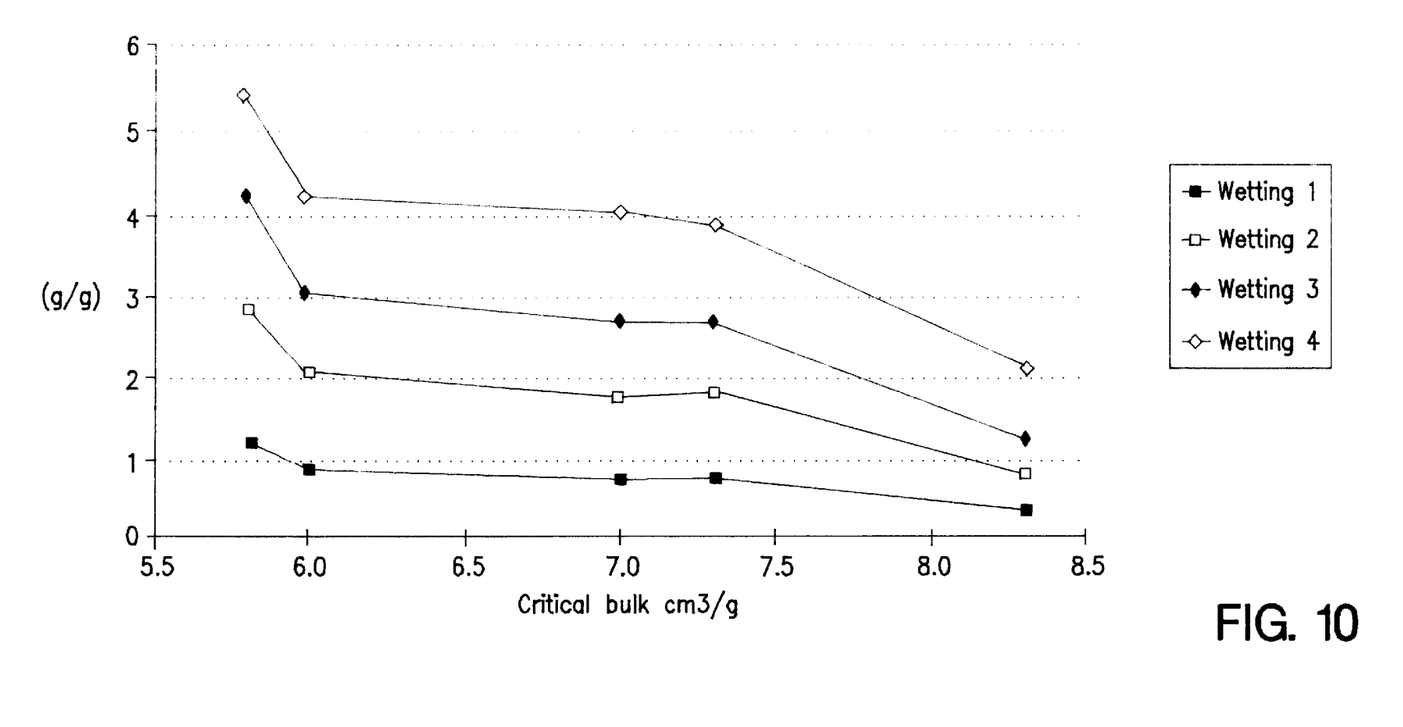
FIG. 10 is a diagram representing the amount of liquid remaining in the upper core at multiple wettings of five different samples having different critical bulks.

Table 3 and the diagram of FIG. 10 show the remaining liquid in the upper core for cellulose fluffs having different critical bulks.

Figure 11:
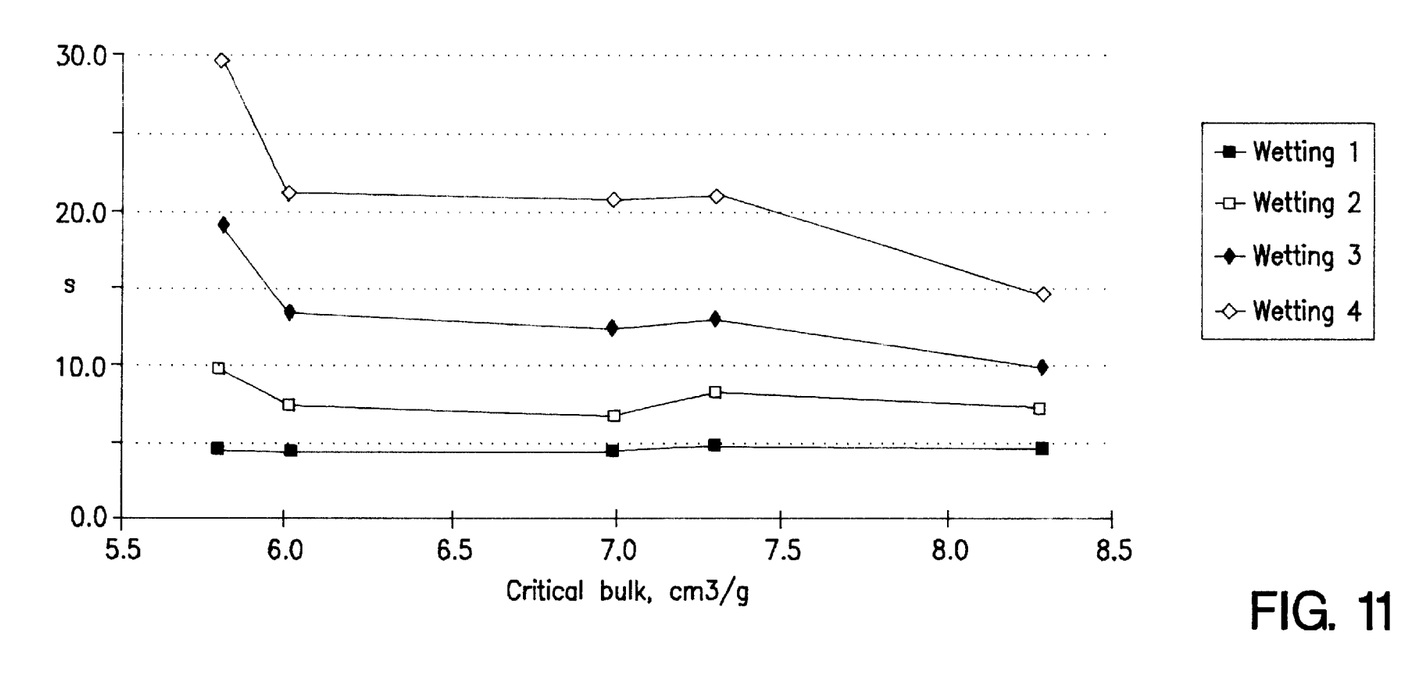
FIG. 11 is a diagram representing the time necessary for the adsorbent body to receive, take up and absorb a given amount of liquid in the upper core of cellulose fluffs having different critical bulks.

Table 4 and the diagram of FIG. 11 show the time necessary for the absorbent body to receive, take up and absorb a given amount of liquid in the upper core for cellulose fluffs having different critical bulks.

Table 5 specifies the different pulp qualities used in tests 1–5 and the critical bulks of these pulp qualities.

TABLE 3

Remaining liquid in the upper core at multiple wettings, g/g

| Sample No | Crit. bulk | Wetting 1 | Wetting 2 | Wetting 3 | Wetting 4 |
| --- | --- | --- | --- | --- | --- |
| 1 | 5.8 | 1.32 | 2.96 | 4.33 | 5.53 |
| 2 | 6.0 | 0.98 | 2.13 | 3.14 | 4.35 |
| 3 | 7.0 | 0.78 | 1.77 | 2.71 | 4.01 |
| 4 | 7.3 | 0.81 | 1.79 | 2.63 | 3.86 |
| 5 | 8.3 | 0.33 | 0.77 | 1.12 | 2.03 |

TABLE 4

Acquisition time at multiple wettings, g/g

| Sample No | Crit. bulk | Wetting 1 | Wetting 2 | Wetting 3 | Wetting 4 |
| --- | --- | --- | --- | --- | --- |
| 1 | 5.8 | 4.8 | 9.8 | 19.1 | 29.5 |
| 2 | 6.0 | 4.7 | 7.4 | 13.5 | 21.1 |
| 3 | 7.0 | 4.5 | 6.4 | 12.4 | 20.3 |
| 4 | 7.3 | 4.8 | 8.0 | 12.9 | 20.7 |
| 5 | 8.3 | 4.3 | 6.5 | 9.6 | 14.5 |

TABLE 5

Critical bulk for different qualities of pulp. $cm^3/g$

| Sample No | Crit. bulk | Labelling | Description | |
| --- | --- | --- | --- | --- |
| 1 | 5.8 | KEA | Vigor fluff EA from Korsnas AB | Chem |
| 2 | 6.0 | WH NB 416 | NB 416 from Weyerhaeuser. | Chem |
| 3 | 7.0 | HBA | HBA from Weyerhaeuser | Chem |
| 4 | 7.3 | SF 70 | SF 70 from Stora AB | CTMP |
| 5 | 8.3 | HTCTMP | HTCTMP from SCA Wifsta-Östrand AB | CTMP |

The results of the measurements show that there are stepwise changes in the function of absorbent structures comprising upper cores of cellulose fluffs with different critical bulks. One step in changing properties is at a critical bulk of about 6 $cm^3/g$ and another step lies at about 8 $cm^3/g$. The diagram of FIG. 10 shows that in an absorbent body an upper core having a critical bulk above 8 $cm^3/g$ is easier to drain than the upper core made of cellulose fluff having a critical bulk beneath 8 $cm^3/g$. The remaining liquid in the upper core will, therefore, be lower. This is especially pronounced at repeated wettings. the diagram of FIG. 11 shows that an absorbent body having an upper core with a critical bulk above 8 $cm^3/g$ more quickly absorbs a given amount of liquid than an absorbent body having an upper core made of cellulose fluff having a critical bulk beneath 8 $cm^3/g$. This also facilitates the above described draining of the upper core. Here also the effect will be greater at repeated wettings.

Thus, when using a lower core having a critical bulk of about 6 $cm^3/g$ and an upper core having a critical bulk of about 5.8 $cm^3/g$, the remaining liquid as well as the acquisition time are essentially higher than when both cores have the same critical bulk or when the upper core has a higher critical bulk than the lower core. When the critical bulk of the upper core increases from 6 $cm^3/g$ to about 7.5 $cm^3/g$ no essential decrease of the remaining liquid or the acquisition time is obtained. Neither does a change from chemical pulp to CTMP in the upper core give any essential improvement.

However, when the critical bulk of the upper core is increased above about 8 $cm^3/g$, a surprising and essential improvement of both the remaining liquid and the acquisition time is obtained. It is therefore essential according to the invention that the critical bulk of the upper core is at least 8 $cm^3/g$ and that the critical bulk of the lower core is beneath 8 $cm^3/g$. Preferably the the second absorbent layer is comprised of fluff having a critical bulk of at most 7 $cm^3/g$ at 2.5 kPa, especially at most 6 $cm^3/g$ at 2.5 kPa.

The invention will now be described in more detail with reference to an exemplifying embodiment illustrated in the accompanying drawings, in which.

Figure 1:
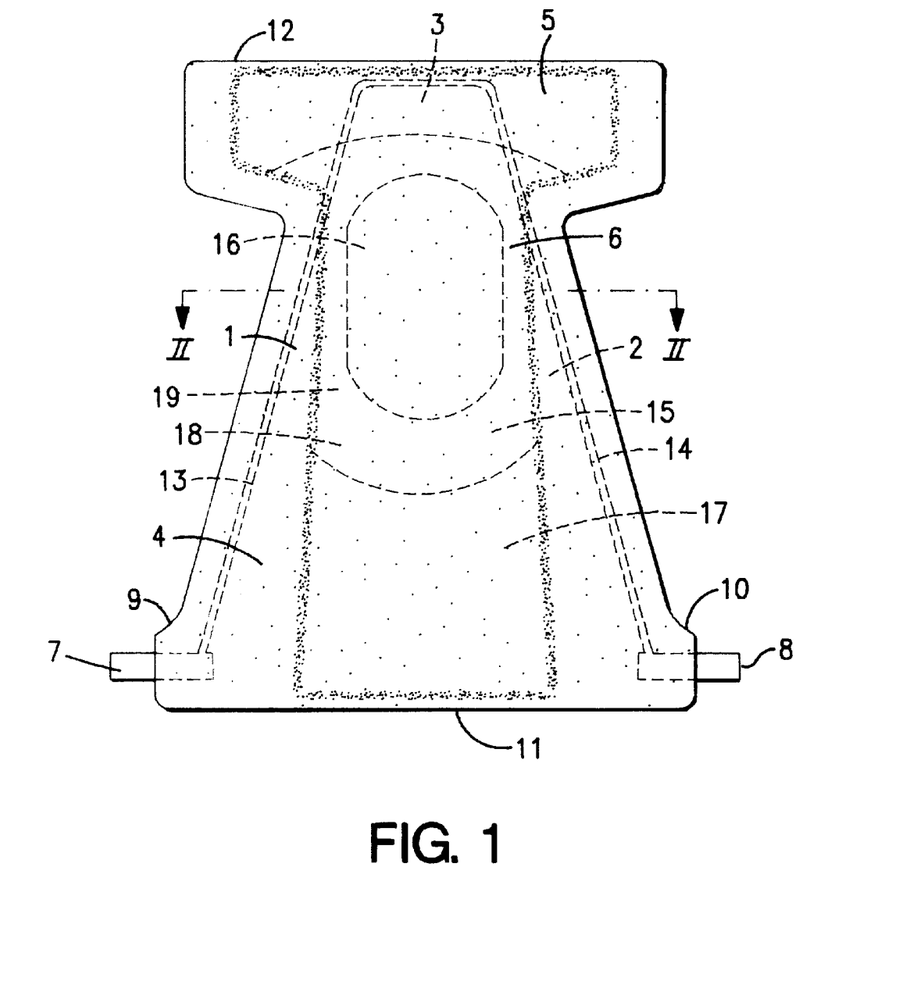
FIG. 1 is a top view of an inventive diaper as seen from the side which faces the wearer in use.

The diaper illustrated in FIG. 1 comprises a liquid-permeable casing sheet 1, made for instance of nonwoven fabric or perforated plastic film, a liquid-impermeable casing layer 2, for instance made of plastic film or a hydrophobic nonwoven fabric, and an absorbent body 3 enclosed in these two layers 1, 2.

The diaper is intended to embrace the lower part of the user's torso in the form of a pair of absorbent pants and is to this end provided with a rear part 4 which, when the article is worn, is intended to face rearwardly on the wearer, a front part 5 which, when the article is worn, is intended to face forwardly on the wearer, and a narrower crotch part 6 which is located between the rear part 4 and the front part 5 and which, in use, is intended to be positioned in the wearer's crotch, between the thighs thereof. In order to enable the diaper to be secured in the desired pants-like configuration, fastener tabs 7, 8 are provided on the two side edges 9, 10 of the rear part 4 close to the rear centre edge 11 of the diaper, said side edges 9, 10 extending in the longitudinal direction of the diaper. In use, the fastener tabs 7, 8 are fastened to the outside of the front diaper part 5, close to the centre edge 12, thereby holding the diaper around the wearer's waist.

The diaper also includes pre-tensioned or pre-stretched elastic devices 13, 14 which extend over the diaper in a V-shaped pattern, with the apex of the V located at the front centre edge 12 of the diaper. The elastic devices 13, 14 may consist of any suitable material whatsoever, such as elastic foam, elastic bands or covered elastic threads. For the sake simplicity, the elastic devices 13, 14 have been shown in a stretched state in FIG. 1. As soon as the stretch or tension in the devices is relieved, the elastic devices will contract, however, to form leg elastications.

Figure 2:
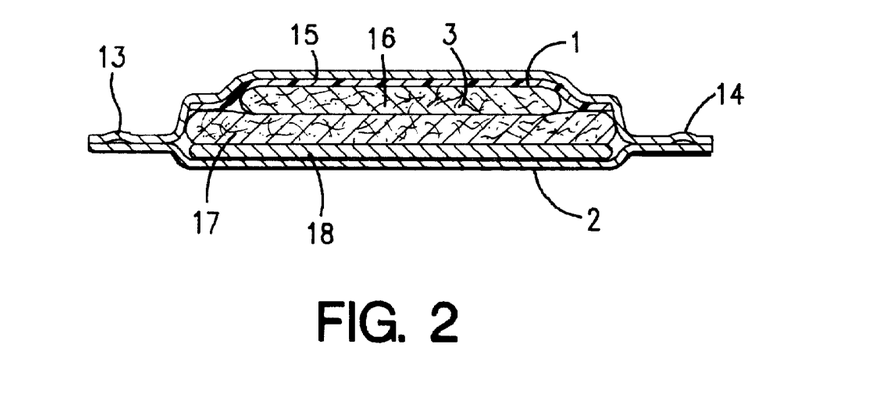
FIG. 2 is a sectional view of the diaper shown in FIG. 1, taken on the line II—II in said Figure.

The diaper absorbent body 3 is composed of a number of different layers. Located nearest the liquid-permeable casing layer I is a thin layer of cellulose fluff 15 which has a high critical bulk, a large pore volume and low liquid-spreading ability. There then follows in a direction towards the liquid-impermeable casing layer 2 a first absorbent layer 16 comprised of cellulose fluff of large pore volume, high wet resilience and low liquid-spreading ability, and a second absorbent layer 17 which is comprised of cellulose fluff of small pore volume, low wet resiliency and high liquid-spreading ability. Both of the aforesaid absorbent layers also include superabsorbent material. Disposed nearest the liquid-impermeable casing layer is a cellulose-fluff isolating layer 18 in which no superabsorbent material is included.

The absorption properties of this layer 18 are less importance, since the layer is mainly intended to prevent superabsorbent material in the second absorbent layer from penetrating into the liquid-impermeable layer. When a diaper is compressed, it is possible for superabsorbent particles which lie in direct contact with the liquid-impermeable casing layer 2 to penetrate said layer and to give rise to small holes through which liquid is able to leak. The cellulose fluff in the insulating or isolating layer 18, however, will preferably have the same properties as the cellulose fluff of the second absorbent layer 17 with regard to liquid-spreading ability and pore volume.

The cellulose fluff layer 15 located nearest the liquid-permeable casing layer 1, and also the second absorbent layer 17 and the isolating layer 18, all have generally the same size and are configured as a T, with the cross member of the T located at the front diaper part 5. On the other hand, the first absorbent layer 16 has an oval shape and is located generally in the crotch part 6 of the diaper, around the so-called wet point. As previously mentioned, the wet point is that region of the diaper surface onto which body liquid, or fluid, is first discharged. As will be understood, it is impossible in practice to establish exactly where this point will be, although it is feasible to anticipate that the body liquid will first meet the diaper within a given restricted area thereon. This area is generally displaced slightly towards the front part of the diaper, both in the case of men and of women Since liquid is only slightly spread in the first absorbent layer 16, it is sufficient for this layer to extend over that region of the diaper in which wetting will more than likely occur.

The first absorbent layer 16 functions as a collecting region for discharged body liquid, or fluid. Because the fibre structure is porous, the liquid is able to penetrate rapidly into the layer 16, where it is collected.

Since the second absorbent layer 17 has finer capillaries than the first absorbent layer, the liquid will be transported by capillary forces to the absorbent layer 17, at a rate which is dependent on the rate at which liquid is spread in the second absorbent layer 17.

The first absorbent layer 16 includes about 10% superabsorbent, calculated on the total weight of the layer when dry. The superabsorbent is distributed substantially evenly in the layer and is intended to absorb and to bind any liquid which remains in the layer, subsequent to the layer having been drained of liquid by the second absorbent layer 17.

Because the first absorbent layer 16 contains superabsorbents, there is obtained an extremely dry surface, since the spaces between respective fibres in the layer are practically emptied completely of liquid.

The cellulose fibres in the second absorbent layer are also admixed with a superabsorbent. The admixture of superabsorbent is restricted, however, to an area 19 which is somewhat larger than the first absorbent layer 16 but which is also restricted essentially to the crotch part 6 of the diaper. The superabsorbent is essentially evenly distributed, however, within the region 19 containing said superabsorbent and reaches to about 20% of the total dry weight of said area.

The superabsorbent in the second absorbent layer is intended to answer for a large part of the absorbency of the layer 17. Furthermore, the superabsorbent binds the absorbed liquid and prevents it from leaking from the diaper when the diaper is subjected to pressure.

Although the aforedescribed exemplifying embodiment refers solely to a diaper, it will be understood that the invention can also be applied to incontinence guards and sanitary napkins.

The superabsorbent used in the absorbent body is not restricted either in form of in chemical composition. For example, the superabsorbent may have the form of flakes, fibres, granules, powder or the like. Various types of superabsorbents may also be used in the various absorbent layers, and the ratio between the superabsorbent concentrations in the two layers may also be varied. For example, it may be suitable to use a superabsorbent of low absorption rate in the first absorbent layer. This will prevent a large part of the liquid taken-up in the first absorbent layer from being absorbed by the second absorbent layer before the superabsorbent has begun to absorb any residual liquid.

It will also be understood that the absorbent body may have any suitable form different to that described with reference to the exemplifying embodiment. Similarly, the relationship between the size and shape of the different layers may also be varied, as can also the thickness of the layers. For example, in the case of certain applications, such as in the case of sanitary napkins and smaller incontinence guards, it may be appropriate to give the first absorbent layer essentially the same extensions as the remainder of the absorbent body.

A number of other modifications are conceivable within the scope of the following claims.

We claim:

1. An absorbent body intended to form the absorbent element of an absorbent article, and comprising a first absorbent layer which, in use, is intended to face towards a wearer, and a second absorbent layer which, in use, is intended to face away from the wearer, said absorbent body including at least two mutually different cellulose fluffs, where the fibre structure of the first absorbent layer is generally comprised of a first type of cellulose fluff having an open structure, a low liquid-spreading ability and a critical bulk which exceeds 8 $cm^3/g$ at 2.5 kPa together with a fibre weight of between 180 and 600 mg/km, and a major part of the fibre structure of the second absorbent layer is comprised of another type of cellulose fluff having a critical bulk beneath 8 $cm^3/g$ at 2.5 kPa together with a fibre weight of between 140 and 190 mg/km and a higher liquid-spreading ability than the cellulose fluff in the first absorbent layer, whereby the second absorbent layer exhibits high ability to drain liquid from the first absorbent layer; said second absorbent layer including superabsorbent material which is admixed generally uniformly in the cellulose fluff within at least one region of the second absorbent layer.

2. An absorbent body according to claim 1, wherein the cellulose fluff in the second absorbent layer has a critical bulk of at most 7 cm$^3$/g at 2.5 kPa.

3. An absorbent body according to claim 1, wherein the cellulose fluff in the second absorbent layer has a critical bulk of at most 6 cm$^3$/g at 2.5 kPa.

4. An absorbent body according to claim 1, wherein the cellulose fluff in the second absorbent layer has a spreading ability which after 10 minutes exceeds 5.5 g/g.

5. An absorbent body according to claim 1, wherein the first absorbent layer includes superabsorbent material which is admixed generally uniformly in the cellulose fluff within at least one region of the first absorbent layer.

6. An absorbent body according to claim 1, wherein the superabsorbent material in the first absorbent layer has a lower absorption rate than the superabsorbent material in the second absorbent layer.

7. An absorbent body according to claim 1, wherein the first absorbent layer has a smaller extension than the second absorbent layer.

8. An absorbent body according to claim 1, wherein the first absorbent layer is comprised generally of a chemithermomechanically produced cellulose fluff; and at least 60% of the second absorbent layer is comprised of a chemically produced cellulose fluff.

9. A diaper comprising an absorbent body enclosed in a casing and having a rear part which, in use, is intended to face rearwardly on a wearer, a front part which, in use, is intended to face forwardly on the wearer, and a crotch part which is located between the rear part and the front part and which, in use, is intended to be located in the crotch region between the wearer's thighs, said absorbent body including at least two mutually different cellulose fluffs; a first isolating layer, a first absorbent layer, a second absorbent layer and a second isolating layer; said second absorbent layer including superabsorbent material distributed generally uniformly within at least one region of said second absorbent layer; and wherein the major part of the fibre structure of the first absorbent layer is comprised of a first type of cellulose fluff having an open structure, a low liquid-spreading ability and a critical bulk which exceeds 8 cm$^3$/g at 2.5 kPa together with a fibre weight of between 180 and 600 mg/km, and a major part of the fibre structure of the second absorbent layer is comprised of another type of cellulose fluff having a critical bulk beneath 8 cm$^3$/g at 2.5 kPa together with a fibre weight of between 140 and 190 mg/km and a higher liquid-spreading ability than the cellulose fluff in the first absorbent layer, whereby the second absorbent layer exhibits high ability to drain liquid from the first absorbent layer.

10. An absorbent body according to claim 9, wherein the cellulose fluff in the second absorbent layer has a critical bulk of at most 7 cm$^3$/g at 2.5 kPa.

11. An absorbent body according to claim 9, wherein the cellulose fluff in the second absorbent layer has a critical bulk of at most 6 cm$^3$/g at 2.5 kPa.

12. A diaper according to claim 9, wherein the first absorbent layer extends over only a part of the surface of the second absorbent layer; and is positioned generally in the crotch part of the diaper.

13. A diaper according to claim 9, wherein the first isolating layer is a layer of cellulose fluff having a critical bulk above 8 cm$^3$/g at 2.5 kPa, and a low liquid-spreading ability.

14. A diaper according to claim 9, wherein the first absorbent layer includes superabsorbent material which is admixed generally uniformly in the cellulose fluff within at least one region of the first absorbent layer.

* * * * *